United States Patent [19]

Wogoman

[11] Patent Number: 4,710,351
[45] Date of Patent: Dec. 1, 1987

[54] AUTOMATED HANDLING SYSTEM

[75] Inventor: Frank W. Wogoman, South Bend, Ind.

[73] Assignee: Miles Laboratories, Inc., Elkhart, Ind.

[21] Appl. No.: 657,940

[22] Filed: Oct. 4, 1984

[51] Int. Cl.$^4$ .......................... B01L 11/00; B65H 5/28
[52] U.S. Cl. ...................................... 422/50; 206/412; 221/72; 221/74; 221/84; 422/99
[58] Field of Search .............................. 422/50, 67, 99; 206/412; 221/78, 77, 71–74, 76, 84

[56] References Cited

U.S. PATENT DOCUMENTS

| 994,916 | 6/1911 | Francis | 221/72 |
|---|---|---|---|
| 3,904,372 | 9/1975 | Lightner | 73/61.1 C |
| 3,918,910 | 11/1975 | Soya et al. | 422/66 |
| 3,980,437 | 9/1976 | Kishimoto et al. | 422/56 |
| 4,218,421 | 8/1980 | Mack, Jr. et al. | 422/56 |
| 4,328,184 | 5/1982 | Kondo | 422/58 |
| 4,337,864 | 7/1982 | McLean | 221/71 |
| 4,437,232 | 3/1984 | Araki et al. | 29/740 |
| 4,453,406 | 6/1984 | Spitzer | 422/66 |
| 4,515,288 | 5/1985 | Atalla | 221/73 |

Primary Examiner—David L. Lacey
Assistant Examiner—C. M. Delahunty
Attorney, Agent, or Firm—R. N. Coe

[57] ABSTRACT

Apparatus and process are disclosed for removing a single flexible member from a storage spool capable of holding multiple flexible members. This storage spool is designed to contain multiple elongated flexible members in an accurate position on the spool by means of radial channels or slots where the flexible members are held in place by interwinding material. By removing the interwinding material on a take up spool the individual flexible member can be positioned for removal from the storage spool by a pick up head or vacuum transport member. The invention has particular applicability to the handling of test devices, such as reagent strips, used in the determination of a biological constituent in a body fluid.

3 Claims, 3 Drawing Figures

AUTOMATED HANDLING SYSTEM

FIELD OF THE INVENTION

The present invention relates to apparatus and process for handling flexible members, especially test devices such as reagent strips used in the determination of constituents present in a liquid sample. More particularly, the invention is concerned with automated vacuum pick up apparatus and a process for removing one flexible member at a time from a storage spool using vacuum pick up apparatus.

BACKGROUND OF THE INVENTION

Increasingly, test devices in the form of reagent strips are being used to provide convenient and rapid analysis of various types of samples, including samples of biological, industrial and automotive fluids, wines and the like. Diagnostic test devices designed for detecting various clinically significant substances or constituents in biological fluids, such as urine and blood, including lysed and unlysed blood, blood plasma and blood serum have in many cases supplanted prior wet chemistry techniques which were both cumbersome and time-consuming. The diagnostic test devices or reagent strips have thus assisted in the fast, inexpensive and accurate diagnosis and treatment of disease.

Conventional test devices generally comprise an absorbent or porous matrix incorporated with indicator reactions, usually of a colorimetric nature. The sample to be tested is contacted with the matrix, such as by momentary emersion, where the sample is liquid, and an indicator response is observed after a period of time. For example, in the detection of occult blood in urine a diagnostic test device can be employed which comprises an absorbent paper impregnated with o-toluidine and peroxide. When this test device is wetted with urine containing occult blood, decomposition of the peroxide occurs with the accompanying oxidation of the o-toluidine to provide a color response. This test is sensitive and extremely useful in diagnosing urinary tract disorders.

For ease in handling, the absorbent or porous matrix, sometimes called a "carrier matrix", is advantageously affixed to an insoluble support member such as an organoplastic strip, e.g., polystyrene, by suitable means such as double-faced adhesive tape. Optically transparent substrate material known as Trycite, polystyrene film made by Dow Chemical Company, is preferred. The support member normally has a thickness of about 0.19 mm, a width of about 5 mm and a length which can vary depending on the intended use, the number of reagent areas present, etc.

Currently, test devices are being made by the Ames Division of Miles Laboratories, Inc. which have lengths of about 85.5 mm and about 82.5 mm. Obviously, based on these dimensions and the materials involved, such test devices tend to be small, elongated and flexible in nature. While these test devices are easily manageable during manual handling operations, automated handling has presented a significant problem.

With the need for automated equipment employing test devices for determining constituents in fluids, especially for performing multiple diagnostic tests, it is essential that a mechanical system be devised which is capable of rapidly, accurately and reliably handling one test device at a time. The removal of a single test device from a cartridge, container or magazine containing multiple test devices to permit the transfer of a single test device to another portion of the system for contact with sample to be tested, is, therefore, a key to automating such testing.

In one very special case, i.e., very small test devices which contain a single reagent area, apparatus has been developed for ejecting one test device at a time from a magazine or cartridge containing multiple test devices of a similar nature. Generally, the substrate for such test devices is only slightly larger than the dimensions of the absorbent matrix, which normally measures about 5 mm by about 10 mm. Typically, such ejection devices contain means for ejecting or pushing a test device from a magazine or container in which multiple test devices are spring loaded or gravity fed such that one test device at a time can be ejected when pressure is applied to the edge of either the bottommost or topmost test device.

For standard test devices having elongated dimensions, as set forth above, however, there is no apparatus available which is totally effective for removing one test device at a time from a cartridge or magazine containing other test devices. Ejection systems employed in the special case of very small test devices are not effective for use with test devices of normal dimensions.

In U.S. Ser. No. 263,033, filed May 13, 1981, now abandoned, test device handling apparatus and a process were disclosed involving a cartridge or magazine holder capable of retaining multiple test devices in stacked position inside the holder by detents located on opposite sides of an opening in the bottom of the holder. By applying vacuum pick up means the bottommost test device in the cartridge or magazine could be bent or flexed sufficiently to cause the bottommost test device to pass over the detents and be removed from the cartridge or magazine while retaining the other test devices in the cartridge or magazine. While the disclosed apparatus and method permitted a single test device to be removed from a holder containing multiple test devices the position and operation of the vacuum pick up means were somewhat critical in order to avoid disruption of the test devices remaining inside the container or cartridge when the bottommost test device was removed from the cartridge. The design of this prior art apparatus resulted in a minimum of vibration. Nevertheless, the system, like other prior art systems, was sensitive to alignment of the reagent test devices. Repeated removal of test devices and the accompanying vibration would sometimes result in test device alignment problems for the vacuum pick up means. Moreover, only a relative small number of test devices could be stored in the cartridges employed in connection with the aforementioned test device handling system. The reason for this is that the configuration of the test devices, which contain one or more reagent matrix areas at one end having a thickness greater than at the other end, caused the test devices to become skewed in the cartridges or containers if an attempt was made to stack a large number of test devices. Accordingly, to avoid alignment problems of the reagent test devices in the containers or cartridges the number of test devices had to be limited to a relatively small number of reagent test devices.

Accordingly, for applications requiring automation there has been a need for foolproof test device handling apparatus capable of removing a single flexible member from a cartridge or magazine such that flexible member can then be transferred to another portion of the system.

SUMMARY OF THE INVENTION

An object of the present invention is to provide means for removing a single flexible member at a time from a storage container having a significant number of flexible members.

Another object of the present invention is to provide for a automatic test device handling system capable of rapidly, accurately and reliably removing a single test device from a container containing multiple test devices.

In accordance with the present invention, flexible member handling apparatus and a process are disclosed which involve a storage spool capable of maintaining multiple flexible devices positioned in channels in accurate radial position with sheet or fabric material interwound between the flexible members so as to effectively segregate each flexible member from the other while holding the flexible members in position in said storage spool. The flexible member storage spool is connected with a take up reel such that the sheet or fabric material interwound with the flexible members can be removed to render one flexible member at a time accessible to vacuum pick up means such that said flexible member can be removed from the storage spool while retaining the other flexible members in said spool.

DESCRIPTION OF THE DRAWINGS

Other and further objects, advantages, and features of the invention will be apparent to those skilled in the art from the following detailed description thereof, taken in conjunction with the accompanying drawings, in which.

DESCRIPTION OF THE PREFERRED EMBODIMENTS

Figure 1:
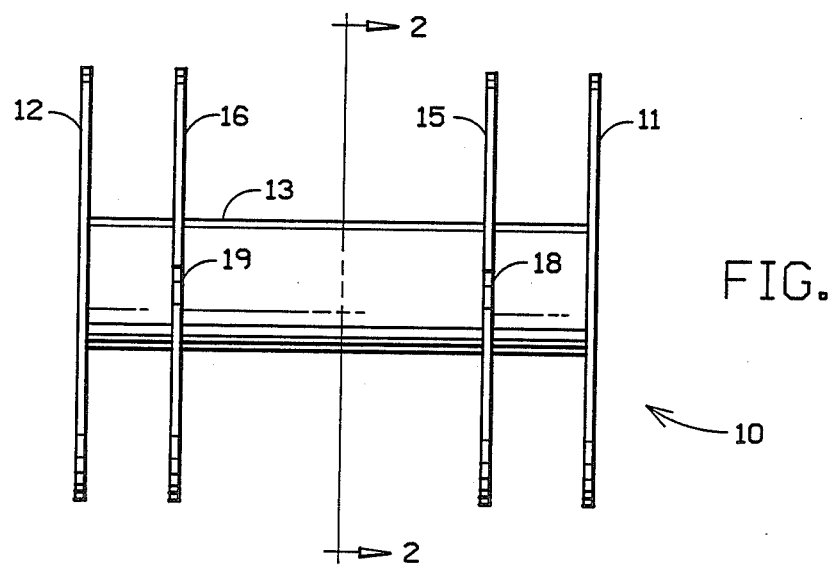
FIG. 1 shows a flexible member storage spool in accordance with the present invention.

In FIG. 1 a reagent strip storage spool 10 is shown comprising circular end walls 11 and 12 separated by and attached to a central core member 13. Located interiorly of end wall members 11 and 12 are circular reagent strip spacer members 15 and 16 which are attached to core member 13. Spacer members 15 and 16 are positioned parallel to each other and to end walls 11 and 12 and spaced from each other as well as from end walls 11 and 12. Spacer members 15 and 16 have multiple radial channels or slots, such as slot 18 on spacer member 15 and 19 on spacer member 16, designed to retain reagent strips parallel to core member 13 lengthways in fixed position in storage spool 10.

Figure 2:
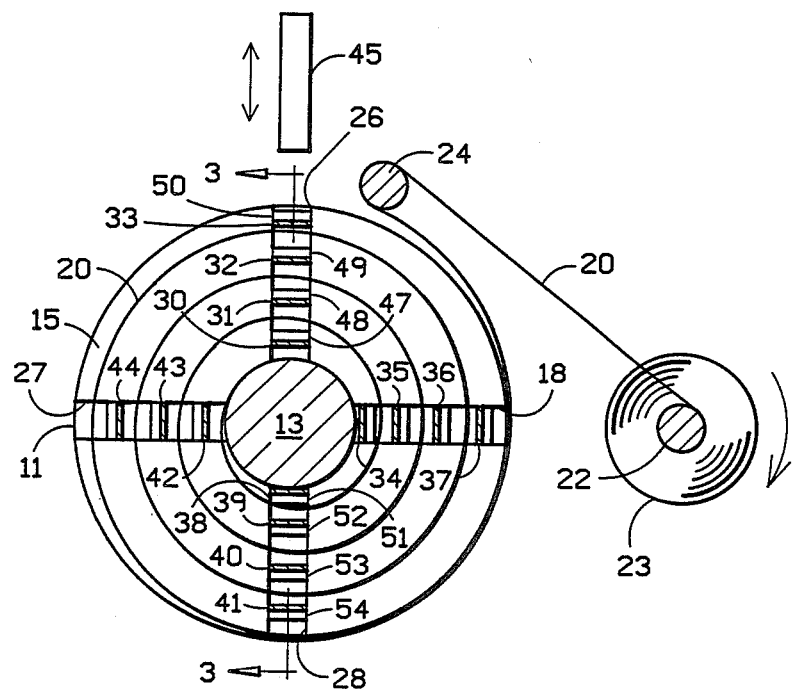
FIG. 2 is a schematic view of the apparatus in FIG. 1 taken along lines 2—2 in which the storage of flexible members in the storage spool is shown, said flexible members being segregated by interwinding material which is interconnected with a take up spool, and vacuum pick up means.

The positioning of reagent strip test devices in storage spool 10 is best illustrated in FIG. 2 which shows reagent test devices present in four slots of spacer member 15 separated from each other by interwinding material 20 which, for purposes of clarity, is illustrated as being separated from the reagent strips rather than in contact with said strips. The interwinding material 20 is wound around core member 13 and between spacer members 15 and 16 so as to effectively hold each reagent strip in place in storage spool 10 while segregating each strip from the next adjacent reagent strip in the same slot. Moreover, the thickness of interwinding material 20 is such as to minimize the skewing effect caused by the variation in thickness of the end of the reagent strip containing the reagent matrix.

Figure 3:
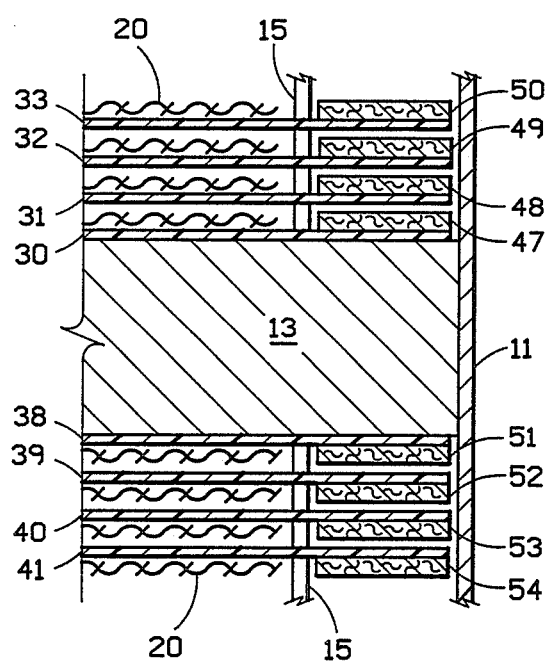
FIG. 3 is an enlarged cross-sectional drawing of the portion of FIG. 2 taken along lines 3—3.

Spacer members 15 and 16 can obviously be adjusted in location with respect to end walls 11 and 12 such that the ends of the reagent strips containing reagent matrices will lie in-between the spacer members and the end walls of the storage spool. Accordingly, as illustrated in FIG. 3, reagent strips can be stacked in each slot of storage spool 10 and held in segregated position substantially flat until the interwinding material 20 is removed exposing one reagent test device at a time for removal from the storage spool 10 by pick up means as hereinafter described.

Referring to FIG. 2 in more detail, end wall 11 and spacer member 15 are shown in which spacer member 15 has four slots (18, 26, 27 and 28) for retaining reagent test devices parallel to core member 13. Thus, reagent test devices comprising substrates 30, 31, 32 and 33 having reagent matrix material 47, 48, 49 and 50, respectively, are present in slot 26 (also see FIG. 3). In like manner slot 28 contains reagent strip substrates 38, 39, 40 and 41 with matrix material 51, 52, 53 and 54, respectively. In similar fashion slot 18 contains reagent test device substrates 34, 35, 36, 37 and slot 27 contains reagent test device substrates 42, 43, and 44.

In operation, interwinding material 20 can be wound around core 22 of take up spool 23 so as to expose reagent test devices present in storage spool 10 sequentially for removal from the storage spool by vacuum pick up means 45. For purposes of maintaining tension on the interwinding material 20 an idler pulley 24 can be employed.

As the take up spool 23 rotates in the direction of the arrow in FIG. 2 interwinding material 20 is wound around core 22 causing storage spool 10 to rotate counter clockwise exposing the topmost reagent test device in slot 26 which is then removed by vacuum pick up means 45. The remaining test devices present in slot 26 are held in place by interwinding material 20. As interwinding material is wound around core 22 of take up spool 23 the topmost reagent strip in slot 18 would next become exposed for removal by pick up means 45. This procedure can be followed until all the reagent strips in all of the slots have been removed. At that time the storage spool can be loaded with new reagent strip test devices by loading the reagent strip test devices segregated by interwinding material 20 which is removed from take up spool 23 by simply reversing the direction of movement of storage spool 10 and take up spool 23.

It will be understood that storage spool 10 can be made from any suitable material, and can be made any desired size. Polymeric materials of propylene, carbonate, styrene, ethylene, butadiene, as well as metals such as aluminum, rubber and other materials are entirely satisfactory. Typically the diameter of the spacer members will be substantially the same as the end walls. Obviously, the number and spacing of the spacer members can be varied depending on the particular type of flexible members held in place. While end members 11 and 12 are not absolutely necessary they are advantageous when transporting the storage spool to prevent the contained flexible members from shifting significantly in the storage spool. Whereas only four slots are illustrated in the drawings as being present in the spacer members, each spacer member can contain any desired number of slots. Normally, however, the number will be in excess of 4 and be divisible by 2. Obviously, the slots on each of the spacer means are aligned such that flexible members, e.g. reagent strip test devices, can be positioned perpendicular to the end walls and parallel to core member 13.

Interwinding material 20 can be any suitable sheet or fabric material which is highly flexible and relatively thin, such as cloth, plastic or metal material, which can effectively be used to segregate one strip from another. It has been found that nylon mesh of substantially the same thickness as the matrix area of a reagent strip is particularly effective for separation of reagent strips. Obviously, the interwinding material should not have a thickness which would take up a considerable amount of space and should not be made from a material which will adhere to or stick to the flexible members.

Pick up means 45 can be operated by known means to move in the direction of the arrows in FIG. 2 to pick up a single reagent strip at a time from storage spool 10. The same vacuum pick up means (i.e., transport means) 45 can be used to sequentially remove flexible members from storage spool 10 or alternatively different pick up heads can be used for the purpose of removing flexible members, such as test devices, from said storage spool. By controlling the rotation of take up spool 23, using a clutch and escapement mechanism (not shown) or any other equivalent type of mechanism, storage spool 10 can be rotated into position for removal of an individual reagent strip from a slot and then momentarily retained in that position to permit the topmost reagent strip to be removed by pick up means 45. Take up spool 23 then rotates a distance sufficient to permit the next reagent strip to be positioned for pick up and removal from storage spool 10. The storage spool or reel can be keyed to a shaft by means of a drive pin (not shown) which will maintain the storage spool in proper mechanical alignment for the vacuum pick up means.

In a preferred embodiment the spacer members have 18 slots into which approximately 450 flexible members, such as reagent strips, are stacked. This embodiment is designed in such a manner that a two inch wide nylon web is wound around the storage spool to retain the flexible members on the spool.

From the foregoing it will be seen that this invention is well adapted to attain all of the ends and objects hereinabove set forth, together with other advantages which are obvious and which are inherent to the system. The present invention permits a single flexible object, such as a test device, to be removed from a container holding multiple flexible objects. While the invention has been described with particularity to test devices, such as reagent strips, it will be understood that the system and handling apparatus can be used for handling other elongated flexible members such as thin metallic, paper or plastic members. The pick up head and storage spool or drum permits systems to be automated by assuring the retrieval and delivery of one flexible member at a time. In contrast to prior art systems which use vacuum in combination with mechanical elements to effect actual segregation of individual flexible members from their mass storage, the present invention utilizes vacuum only to effect a transfer of an individual flexible member out of the storage means since actual segregation is performed by mechanical means as a result of the design of the system. Accurate radial positioning of the flexible members is achieved by positioning one slot at a time in sequence under the pick up means. Significantly, the present invention provides means for automating reagent strip handling or the handling of other flexible members without requiring a different strip format.

By applying automation to the operation of supplying individual test devices or flexible elements, the following advantages, inter alia, are achieved: elimination of human error and reduction of manpower requirements resulting in the utilization of technicians to perform other duties and the extension of "working hours" available for testing into totally unattended periods during nights and weekends.

The present system also compensates for the actual loading of more than one flexible member or reagent strip in a given position since the excess or duplicate reagent strip will simply be removed by gravity from the storage spool as the storage spool rotates. The vacuum pick up means will only pick up the topmost flexible member.

Due to the type of system involved, the system is capable of being totally automated and controlled by computer.

Obviously, many other modifications and variations of the invention as hereinbefore set forth can be made without departing from the spirit and scope of the invention.

What is claimed is:

1. Storage spool apparatus for storing and dispensing multiple flexible test devices having a reagent matrix attached to substrate material, said storage spool apparatus comprising:
   a storage spool having at least two wall members extending radially from a central core member, said wall members having multiple channels constructed and arranged for retaining flexible test devices parallel to said central core member;
   interwinding material wound around the central core member and between two wall members for retaining flexible test devices in said multiple channels while segregating a flexible test device from a next adjacent parallel flexible test device in the same channel;
   a take-up spool interconnected to said storage spool by attachment to one end of said interwinding material such that rotation of said take-up spool rotates said storage spool and sequentially exposes successive flexible test devices by removing interwinding material from over successive flexible test devices located in said multiple channels of said storage spool;
   vacuum pickup head means mounted adjacent to said storage spool;
   reciprocating means for moving said vacuum pickup head means into said storage spool between said wall members when said storage spool is in a stationary position to contact a flexible test device exposed by rotation of said take-up spool and removing said pickup head means from said storage spool following such contact; and
   means for supplying vacuum to said vacuum pickup head means when said vacuum pickup head means is in contact with a flexible test device in said storage spool.

2. The apparatus of claim 1 in which the interwinding material is flexible.

3. The apparatus of of claim 1 in which the interwinding material is nylon fabric.

* * * * *